(12) United States Patent
Vandewalle et al.

(10) Patent No.: US 11,576,792 B2
(45) Date of Patent: Feb. 14, 2023

(54) QUICK CONNECT THREAD LOCKING MECHANISM AND CAM

(71) Applicant: Zimmer, Inc., Warsaw, IN (US)

(72) Inventors: Daniel Vandewalle, Warsaw, IN (US); Jamie D. Winchester, Warsaw, IN (US); Joshua Clements, Fort Wayne, IN (US); Mallory Wells Kubik, Warsaw, IN (US); Cori Fidler, Warsaw, IN (US); Colton Myers, Warsaw, IN (US); Phillip Michaelson, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 9 days.

(21) Appl. No.: 17/154,071

(22) Filed: Jan. 21, 2021

(65) Prior Publication Data

US 2021/0259853 A1    Aug. 26, 2021

Related U.S. Application Data

(60) Provisional application No. 62/980,733, filed on Feb. 24, 2020.

(51) Int. Cl.
*A61F 2/46* (2006.01)
*A61F 2/34* (2006.01)

(52) U.S. Cl.
CPC .............. *A61F 2/4609* (2013.01); *A61F 2/34* (2013.01); *A61F 2002/4627* (2013.01); *A61F 2002/4629* (2013.01); *A61F 2002/4681* (2013.01)

(58) Field of Classification Search
CPC .. A61F 2/34; A61F 2/4609; A61F 2002/4627; A61F 2002/4629; A61F 2002/4681
See application file for complete search history.

(56) References Cited

U.S. PATENT DOCUMENTS

| | | | | |
|---|---|---|---|---|
| 8,277,457 B1* | 10/2012 | Burgi | ................... | A61F 2/4609 606/81 |
| 2009/0192515 A1* | 7/2009 | Lechot | ................. | A61F 2/4609 606/91 |

* cited by examiner

*Primary Examiner* — Brian A Dukert
(74) *Attorney, Agent, or Firm* — Schwegman Lundberg & Woessner, P.A.

(57) ABSTRACT

Disclosed herein are a system and method for attaching an implant, such as an acetabular cup, to an adapter connector without requiring rotation of the connector or the implant, to allow for easy connection, manipulation, and insertion of the implant into a patient. An adapter connector or adapter inserter can include a collet and a collet spreader. The collet can include an exterior surface and an interior surface. The exterior surface can define a protuberance sized to engage an indentation in an adapter. The interior surface can define a collet cavity. The collet spreader can be located at least partially within the collet cavity. The collet spreader can include a flared surface and an engagement surface. The flared surface can be located at a first end of the collet spreader and arranged to engage the interior surface of the collet so as to cause the collet to expand.

19 Claims, 5 Drawing Sheets

QUICK CONNECT THREAD LOCKING MECHANISM AND CAM

PRIORITY CLAIM

The present application claims the benefit of priority to U.S. Provisional Application No. 62/980,733, filed Feb. 24, 2020, the contents of which is hereby incorporated by reference in its entirety.

FIELD OF THE DISCLOSURE

The present disclosure relates to adapters. Specifically, the present disclosure relates to adapter connectors, adapter inserters, and methods of use thereof.

BACKGROUND

A prosthesis or implant can be positioned in an anatomy, such as a human patient, for various purposes. For example, a prosthesis can be positioned to replace an articulating portion of a joint. For example, an acetabular cup can be placed in an acetabulum during a hip arthroplasty procedure. To install acetabular cups adapter inserters can be used. The adapter inserters can grip the acetabular cup and allow a surgeon to implant the acetabular cup. While reference is made to an acetabular cup, other implants can be used with the devices disclosed herein, including, for example, glenoid implants in shoulder surgery.

SUMMARY

The following, non-limiting examples, detail certain aspects of the present subject matter to solve the challenges and provide the benefits discussed herein, among others.

Example 1 is a system for implanting an acetabular cup implant, the system comprising: a body including a first end; a first linkage coupled to the body at the first end; a collet connectable to the first end of the body, the collet including an exterior surface and an interior surface, the exterior surface defining a protuberance sized to engage an indentation in an adapter, the interior surface defining a collet cavity; and a collet spreader connectable to a first end of the first linkage, the collet spreader including a flared surface located at a first end of the collet spreader and arranged to contact the interior surface of the collet upon retraction of the collet spreader into the collet cavity, wherein, upon retraction of the collet spreader into the collet cavity, the collet expands and the protuberance engages the indentation in the adapter.

In Example 2, the subject matter of Example 1 optionally includes a first cam connected to the first linkage.

In Example 3, the subject matter of any one or more of Examples 1-2 optionally include a lever connected to the body; a second cam; and a second linkage coupling the first cam to the second cam, wherein actuation of the lever causes rotation of the first cam via movement of the second linkage and the second cam.

In Example 4, the subject matter of any one or more of Examples 1-3 optionally include a biasing element located within the collet cavity and arranged to exert an outward force on the collet spreader.

In Example 5, the subject matter of any one or more of Examples 1-4 optionally include wherein the interior and exterior surfaces of the collet define: a plurality of slots proximate a first end of the collet; and a relief opening at a base of each of the plurality of slots.

In Example 6, the subject matter of any one or more of Examples 1-5 optionally include wherein the protuberance is a helical thread.

In Example 7, the subject matter of any one or more of Examples 1-6 optionally include wherein the protuberance is one of a plurality of protuberances.

Example 8 is an adapter inserter comprising: a body having a proximal end and a distal end; a first linkage located at the distal end; a second linkage extending from the proximal end to the distal end; a first cam connecting the first linkage to the second linkage; a lever connected to the body and defining a second cam connected to the second linkage; a collet spreader connected to the first linkage and comprising a flared surface located at a first end of the collet spreader; and a collet connected to the distal end of the body and encircling a portion of the collet spreader, the collet comprising: a protuberance extending from an exterior surface and sized to engage an indentation in an adapter, and an interior surface defining a collet cavity.

In Example 9, the subject matter of Example 8 optionally includes a biasing element located within the collet cavity and arranged to exert an outward force on the collet spreader.

In Example 10, the subject matter of any one or more of Examples 8-9 optionally include wherein the interior and exterior surfaces of the collet define: a plurality of slots proximate a first end of the collet; and a relief opening at a base of each of the plurality of slots.

In Example 11, the subject matter of any one or more of Examples 8-10 optionally include wherein the protuberance is a helical thread.

In Example 12, the subject matter of any one or more of Examples 8-11 optionally include wherein the protuberance is one of a plurality of protuberances.

Example 13 is an adapter connector comprising: a collet including: an exterior surface defining a protuberance sized to engage an indentation in an adapter, and an interior surface defining a collet cavity, and a collet spreader located at least partially within the collet cavity, the collet spreader including: a flared surface located at a first end of the collet spreader and arranged to engage the interior surface of the collet so as to cause the collet to expand, and an engagement surface located at a second end of the collet spreader and configured to connect to an adapter inserter.

In Example 14, the subject matter of Example 13 optionally includes wherein the protuberance is a helical thread.

In Example 15, the subject matter of any one or more of Examples 13-14 optionally include wherein the protuberance is one of a plurality of protuberances.

In Example 16, the subject matter of any one or more of Examples 13-15 optionally include a biasing element sized to fit within the collet cavity.

In Example 17, the subject matter of any one or more of Examples 13-16 optionally include wherein the collet includes at least one thread located at a proximal end of the collet, the at least one thread configured to engage complementary threads of the adapter inserter.

In Example 18, the subject matter of any one or more of Examples 13-17 optionally include wherein the engagement surface defines threads configured to engage complementary threads of the adapter inserter.

In Example 19, the subject matter of any one or more of Examples 13-18 optionally include wherein the interior and exterior surfaces of the collet define a plurality of slots proximate a first end of the collet.

In Example 20, the subject matter of Example 19 optionally includes wherein the interior and exterior surfaces of the collet further define a relief opening at a base of each of the plurality of slots.

Example 21 is a method for implanting an acetabular cup implant in a patient, the method comprising: obtaining or providing the acetabular cup implant; obtaining or providing an adapter inserter comprising a collet and a body, the collet connectable to a first end of a body of the adapter inserter placing a protuberance of the collet into a recess of the acetabular cup; securing the acetabular cup to the collet by rotating a lever of the adapter inserter from an unlocked position to a locked position without rotating the adapter inserter or the collet; striking an impact head of the adapter inserter to implant the acetabular cup in the patient, disengaging the collet from the acetabular cup by rotating the lever of the adapter inserter from the locked position to the unlocked position.

In Example 22, the subject matter of Example 21 optionally includes wherein securing the acetabular cup to the collet by rotating the lever comprises retracting a collet spreader into a collet cavity defined by the collet, thereby causing the collet to expand.

In Example 23, the subject matter of any one or more of Examples 21-22 optionally include wherein securing the acetabular cup to the collet by rotating the lever cause an exterior surface of a collet spreader to contact an interior surface of the collet, thereby causing the collet to expand.

In Example 24, the subject matter of any one or more of Examples 21-23 optionally include wherein securing the acetabular cup to the collet by rotating the lever comprises causing a flared surface located at a first end of a collet spreader to contact an interior surface of the collet, thereby causing the collet to expand.

In Example 25, the subject matter of any one or more of Examples 21-24 optionally include wherein securing the acetabular cup to the collet by rotating the lever comprises causing the acetabular cup to be pulled towards the first end of the body of the adapter inserter.

In Example 26, the subject matter of any one or more of Examples 21-25 optionally include wherein placing the protuberance of the collet into the recess of the acetabular cup does not require rotation of the adapter inserter or the acetabular cup.

In Example 27, the subject matter of any one or more of Examples 21-26 optionally include wherein disengaging the collet from the acetabular cup by rotating the lever from the locked position to the unlocked position comprises causing a portion of a collet spreader contacting an interior surface of the collet to protrude from a distal end of the collet.

In Example 28, the subject matter of any one or more of Examples 21-27 optionally include withdrawing the adapter inserter from the patient, thereby leaving the acetabular cup within the patient.

In Example 29, the systems, adapter connectors, adapter inserters, or method of any one or any combination of Examples 1-28 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

Figure 1A:
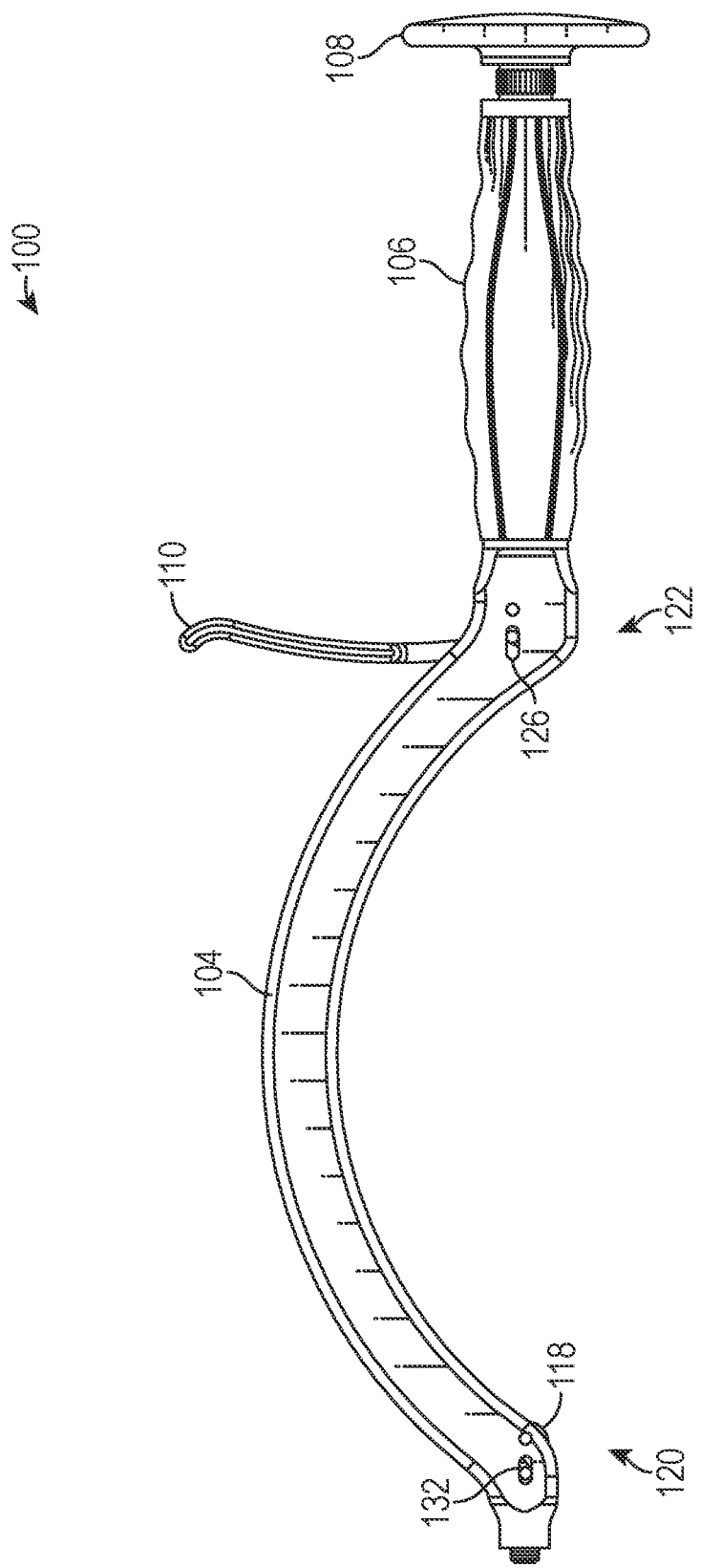
FIG. 1A shows an adapter inserter for inserting an acetabular cup in accordance with at least one example of the present disclosure.

Disclosed herein are adapter connectors, adapter inserters, and methods of use thereof. The adapter connectors disclosed herein can allow the adapter inserters to lock into a thread without requiring rotation, thus overcoming clamping length variations, which can be due to variability in the thread orientation relative to the connectors found on traditional adapter inserters. As disclosed herein, the adapter connectors and adapter inserters can allow for a quick connection to be made to a thread, such as a female thread, along with a robust locking mechanism that prevents the threaded piece from backing out.

The adapter connectors and adapter inserters disclosed herein can include a collet and a collet spreader. The collet and collet spreader can allow connectors disclosed herein to lock into an indentation, such as a female thread, on an adapter without requiring rotation of the connector, which can include a protuberance, such as a male thread. The collets disclosed herein, can be locked outward by the collet spreader as the collet spreader is drawn in toward the body of an adapter inserter. The adapter inserter can draw the cup of an adapter tight to an end of the inserter without regard to the orientation the protuberance due to a linkage and cam mechanism of the inserter. Stated another way, the linkage and cam mechanism coupled with the adapter connector can compensate for variations in initial distance between a female threaded cup and the inserter body.

The linkage and cam mechanism can generate a linear pulling force on the collet spreader. As disclosed herein, the cam action can be achieved via a variable arc length formed around a lever of the adapter inserter. The linear pull cam can transform the rotational motion from a linkage into a linear motion of the collet spreader. The linear pull cam can also serve to ground out tension forces straight back through one or more pivot pins. This can eliminate tendencies for the linkage to cam open during impaction and/or extraction. In other words, the linear pull cam can work with linkages in either compression or extension.

The collets disclosed herein can have a major diameter that is smaller than the male thread found on traditional adapter connectors while still able to couple to the female thread minor diameter of the adapter. The collets can have a rounded "sinusoid" thread profile. The thread profile can allow the collet to collapse and move past female thread minor diameter of the adapter when the collet spreader is in an unlocked position. Upon locking the collet spreader in a locked position, the collet can engage the female threads of the adapter so as to prevent the collet from pulling past the female threads during extraction and/or reversion impaction.

The collet can have a tapered geometry to match the collet spreader. The collet spreader can expand and lock to the adapter. Once locked to the adapter, the collet can pull the adapter tight against a surface of the adapter inserter.

The collet spreader can have an angled surface at a first end of the collet spreader. The angled surface can contact an inner surface of the collet to expand the collet thereby locking the collet to the adapter while the collet spreader is being retracted. Tension can run through the collet, the collet spreader, and the linkage to the linear cam puller, where it grounds out to the inserter body via the pivot pin.

While this disclosure describes the adapter connectors and adapter inserters with respect to insertion of adapters for acetabular cups, the adapter connectors and adapter inserters are not limited to acetabular cup insertion. The ability to lock into a thread without turning a male thread, and to overcome axial variation using the collets, collet spreaders, cams, and linkages disclosed herein can be applied to various applications where one wants to quickly mate to a threaded joint without requiring rotation or "clocking" of the adapter inserter.

The above discussion is intended to provide an overview of subject matter of the present patent application. It is not intended to provide an exclusive or exhaustive explanation of the embodiments disclosed herein. The description below is included to provide further information about the embodiments.

Figure 1B:
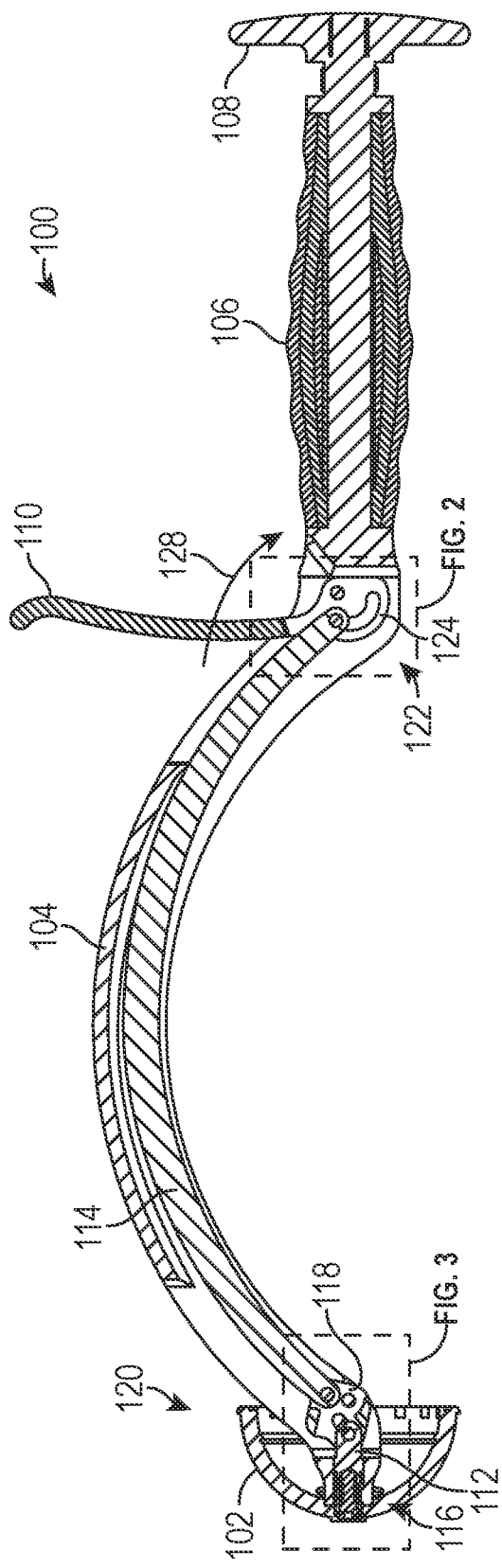
FIGS. 1B and 1C show cross-sectional views of the adapter inserter of FIG. 1A in accordance with at least one example of the present disclosure.
Figure 1C:
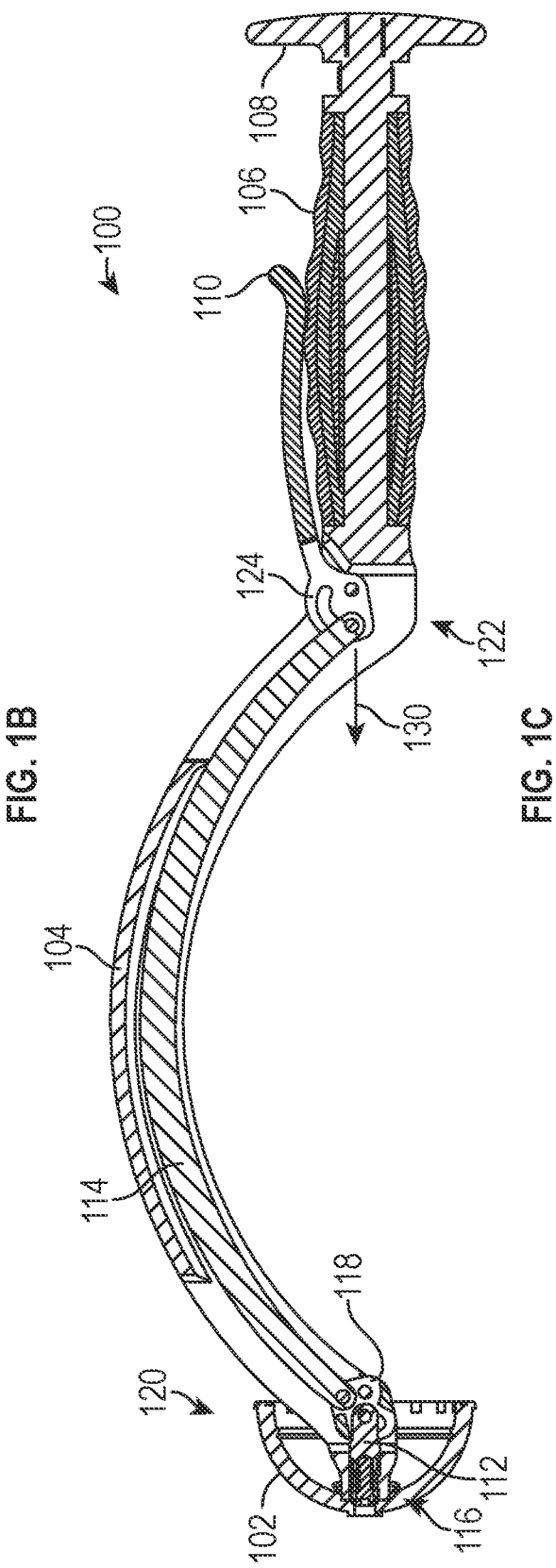

FIGS. 1A, 1B, and 1C illustrate an adapter inserter 100 for inserting an acetabular cup 102, in accordance with at least one example of this disclosure. Adapter inserter 100 can include a body 104, a handle 106, an impaction head 108, lever 110, a first linkage 112, a second linkage 114, and an adapter connector 116. A cam 118 can connect first linkage 112 to second linkage 114. Adapter connector 116 can be connected to body 104 at a first, or distal, end 120 of body 104. Handle 106 and lever 110 can be connected to body 104 at a second, or proximal, end 122 of body 104. Impaction head 108 can be connected to handle 106. Impaction head 108 can be removable or permanently attached to handle 106.

Figure 2:
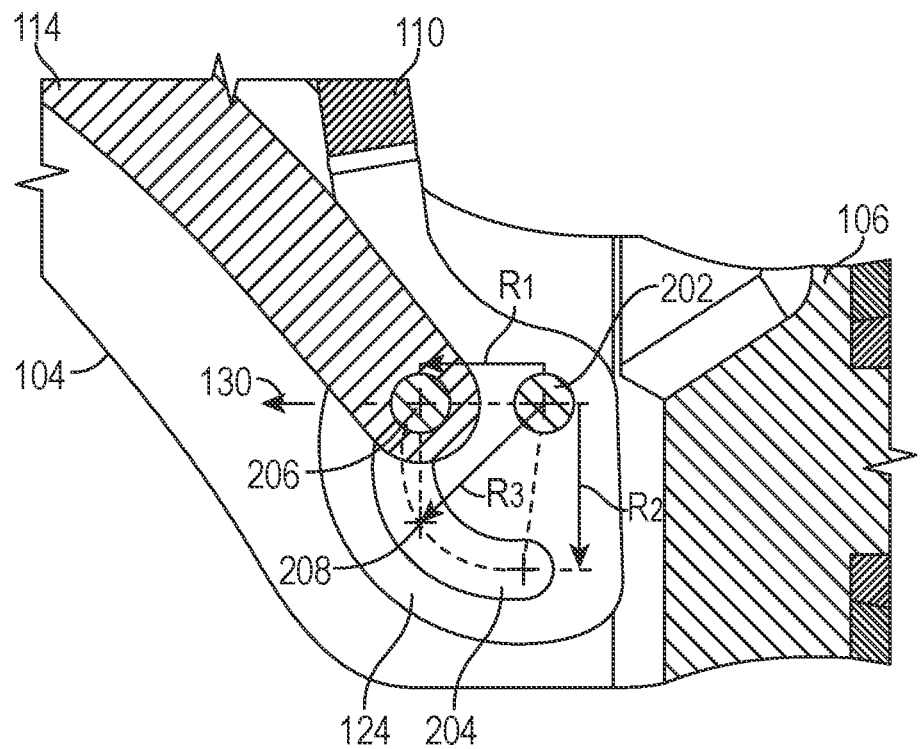
FIG. 2 shows a detailed view of a portion of the adapter inserter identified in FIG. 1B in accordance with at least one example of the present disclosure.

As shown in FIGS. 1B and 1C, lever 110 can be positioned in an unlocked state (FIG. 1B) and a locked state (FIG. 1C). Lever 110 can form a second cam 124. As shown in FIG. 2, cam 124 can include a pivot pin 202 and define a slot 204. A translation pin 206 can translate within slot 204 as lever 110, and by extension cam 124, are rotated about pivot pin 202. Slot 204 can have a first radius, $R_1$, which can correspond to lever 110 being in the unlocked state. A second radius, $R_2$, can correspond to lever 110 being in the locked state. At portions of slot 204 in between the locked and unlocked state, slot 204 can have a third radius, $R_3$.

The first radius, second radius, and third radius can each be different. For example, the third radius can be greater than the first and second radii. The first radius can be greater or less than the second radius. The radius of slot 204 can vary continuously from the locked state to the unlocked state. By having the third radius, or the radius of slot 204 in between the locked and unlocked states, be greater than the first and second radii, lever 110 can be locked or otherwise be secured in the locked and unlocked states as explained below.

Body 104 can define a slot 126 (see FIG. 1A) for which translation pin 206 can translate. Thus, as lever 110 is rotated from the unlocked position to the locked position as indicated by arrow 128, the motion of translation pin 206 is constrained to a linear motion. As a result, rotation of lever 110 as indicated by arrow 128 can cause second linkage 114 to translate as indicated by arrow 130.

Embodiments disclosed herein can allow for either compression (push) or tension (pull) to lock cup 102 to adapter inserter 100. For example, as shown here, slot 316 allows for a linkage 114 to compress against came 118 to lock cup 102 to adapter inserter 100. For a tension arrangement, slot 316 can be flipped to allow linkage 114 to be in tension thereby locking cup 102 to adapter inserter 100.

When in the locked state, there can be tension or compression on second link 114, which can further cause lever 110 to be biased in the direction of arrow 128 due to transition pin 206 being located along a line of action that does not pass through pivot pin 202. Stated another way, in the locked position, a tension force on transition pin 206 in the direction opposite arrow 130 can cause cam 124 to create a moment about pivot pin 202 thereby biasing lever 110 towards handle 106.

Figure 3:
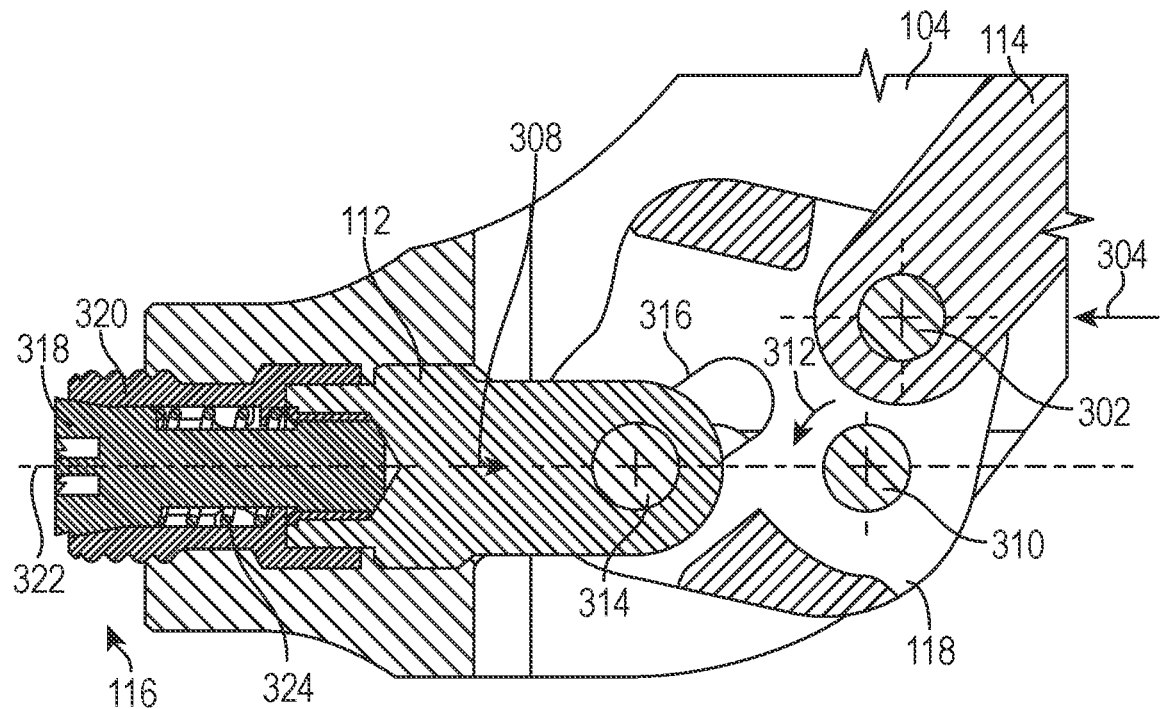
FIG. 3 shows a detailed view of another portion of the adapter inserter identified in FIG. 1B in accordance with at least one example of the present disclosure.

As disclosed herein, movement of lever 110 from the unlocked state to the locked state can cause second linkage 114 to move as indicated by arrow 130. As shown in FIG. 3, movement of second linkage 114 as indicated by arrow 130 can cause movement of a transition pin 302 as indicated by arrow 304. As shown in FIG. 1A, body 104 can define a slot 132 that can restrict motion of a transition pin 314 as indicated by arrow 308. Thus, when second linkage 114 moves as indicated by arrow 304, first cam 118 can rotate about pivot pin 310 as indicated by arrow 312. Rotation of first cam 118 as indicated by arrow 312 or contra to arrow 312 can cause translation pin 314 to move within a slot 316 in first cam 118. By restricting motion of translation pin 314 in the direction of arrow 308, first linkage 112 can cause motion of a collet spreader 318 in the direction of arrow 308.

As an example, and as shown in FIG. 2, as lever 110 is rotated from the unlocked position to the locked position, slot 204 can initially get farther away from pivot pin 202 (i.e., $R_3$ increases to be greater than $R_1$) to compress the second linkage 114. During a last portion of the arc formed by slot 204 as lever 110 travels to locked position the distance from the pivot reduces slightly (i.e., $R_3$ decreases to $R_2$) to allow second linkage 114 to expand slightly and thereby causing second cam 124 to cam over past top-dead-center 208. In the locked position, the distance transition pin 206 is from pivot pin 202 (i.e., $R_2$) can be greater than when transition pin 206 is in the unlocked position (i.e., $R_1$). The inverse can be done if it is desirable to stretch second linkage 114.

Adapter connector 116 can include collet spreader 318 and a collet 320. As disclosed herein, movement of collet spreader 318 along a central axis 322 can retract collet spreader 318 into collet 320. As collet spreader 318 is retracted into collet 320, collet spreader 318 can contact collet 320. Contact between collet spreader 318 and collet 320 can cause collet 320 to expand and contact an adapter for, or a portion of, cup 102. The contact between collet 320 and cup 102 can secure cup 102 to adapter inserter 100 as disclosed herein.

As disclosed herein, movement of lever 110 into the locked position can cause collet spreader 318 to retract into collet 320. As lever 110 is moved to the unlocked position, tension on second linkage 114 can be released, which in turn can release tension on first cam 118. The relaxation of tension on first cam 118 can allow a biasing element 324 to apply a force to collet spreader 318 opposite the direction of arrow 308. The force applied to collet spreader 318 by biasing element 324 can cause collet spreader 318 to relieve pressure on collet 320, thereby allowing release of cup 102 from adapter inserter 100.

Figure 4:
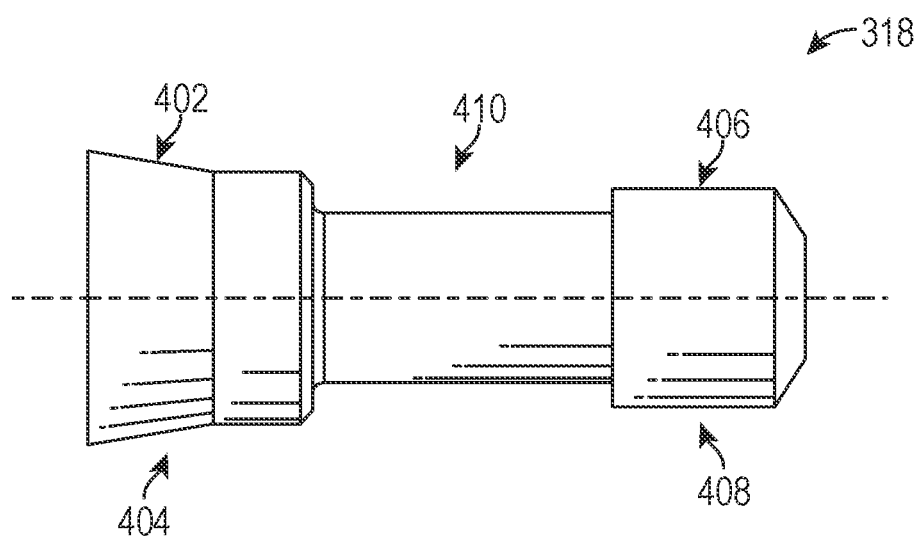
FIG. 4 shows a collet spreader in accordance with at least one example of the present disclosure.

FIG. 4 shows collet spreader 318 in accordance with at least one example of the present disclosure. Collet spreader 318 can include a flared surface 402 located at a first, or distal, end 404 of collet spreader 318. Collet spreader 318 can include an engagement surface 406 located at a second, or proximal, end 408 of collet spreader 318. Engagement surface 406 can include treads or other protrusions that allow collet spreader 318 to connect to first linkage 112.

Collet spreader 318 can also include a recessed portion 410. Recessed portion 410 can be used to accommodate biasing element 324. For example, biasing element 324 can be a compression spring that encircles recessed portion 410.

Figure 5A:
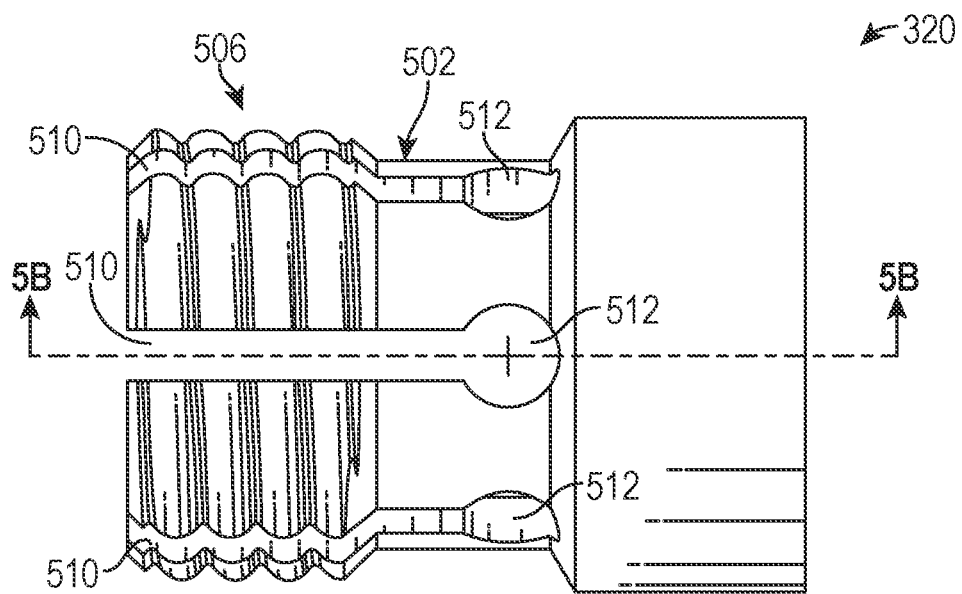
FIGS. 5A and 5B show a collet and a section view of the collet in accordance with at least one example of the present disclosure.
Figure 5B:
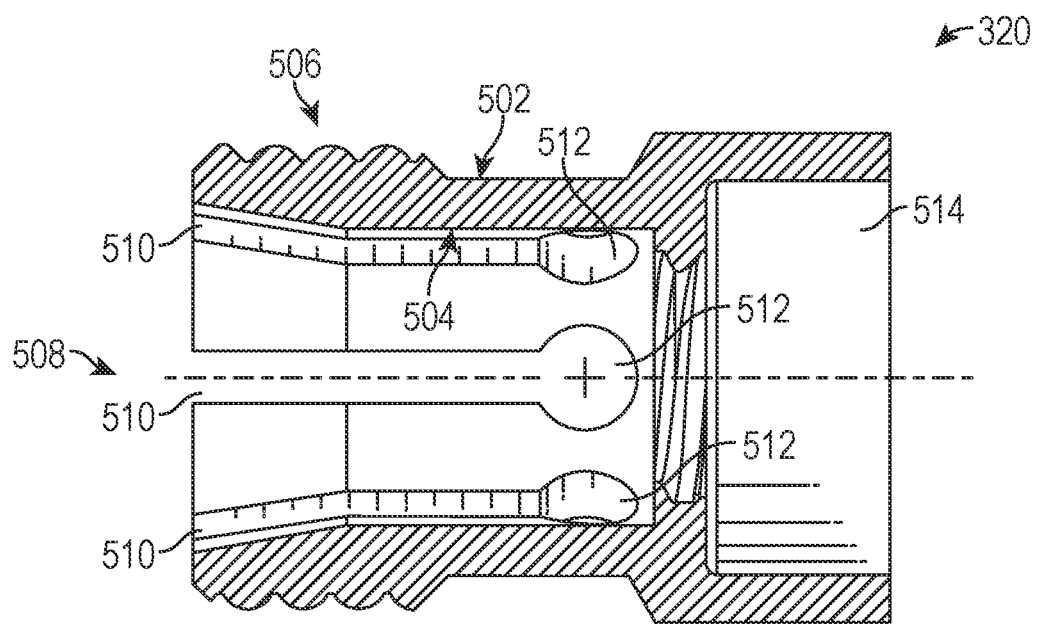

FIG. 5A shows collet 320 and FIG. 5B shows a section view of collet 320, each in accordance with at least one example of the present disclosure. Collet 320 can include an exterior surface 502 and an interior surface 504. Exterior surface 502 can define one or more protuberances 506 sized to engage an indentation in an adapter or cup 102. For example, as shown in FIGS. 5A and 5B, protuberances 506 can be helical threads that engage complementary threads in cup 102.

Interior surface 504 can define a collet cavity 508. Collet cavity 508 can be sized to allow collet spreader 318 to be located at least partially within collet cavity 508. For example, collet spreader 318 can be partially inserted into collet cavity 508 so that flared surface 402 can contact interior surface 504 as collet spreader 318 is retracted into collet cavity 508 via motion of lever 110. The contact between interior surface 504 and flared surface 402 can cause collet 320 to expand so that protuberances 506 contact cup 102.

Exterior surface 502 and interior surface 504 can define one or more slots 510. Slots 510 can provide flexibility so that collet 320 can expand and contract as collet spreader 318 passes into and out of collet cavity 508. Each of slots 510 can include a relief opening 512 located at a base of slots 510. Relief openings 512 can provide for stress relief and/or reduce stress concentrations that can develop due to the expansion and contraction of collet 320.

Collet 320 can also include an engagement section 514. Engagement section 514 can allow collet 320 to couple to first linkage 112. For example, as shown in FIG. 3, collet 320 can encircle a portion of first linkage 112. Collet 320 can be free floating. Collet spreader 318 can be screwed or otherwise connected to first linkage 112, resulting in collet 320 being constrained between first linkage 112 and flared surface 402. Thus, when collet spreader 318 is retracted into collet cavity 508, collet 320 can retract into body 104 to pull cup 102 into contact with adapter inserter 100.

As disclosed herein, protuberances 506, such as male threads, can have a major diameter that is smaller than a complementary indentation, such as female threads, of cup 102 while still having some interference with the complementary indentation. The interference can allow cup 102 to be loosely attached to adapter inserter 100.

Protuberances 506 can define a rounded "sinusoid" thread profile as shown in FIGS. 5A and 5B. The sinusoid profile can allow protuberance 506 to collapse and move past female threads of cup 102 when lever 110 is in the unlocked position (i.e., flared surface 402 is not in contact, or in compression, with interior surface 504). Once cup 102 is loosely attached to collet 320, lever 110 can be rotated from the unlocked position to the locked position as disclosed herein, thereby securing cup 102 to collet 320.

Adapter inserter 100, including collet spreader 318 and collet 320, can be made of metals, polymers, ceramics, or combinations thereof. In addition, adapter inserter 100 can be manufactured using a variety of manufacturing techniques including, but not limited to, machining, injection molding, overmolding, etc. For example, collet spreader 318 and/or collet 320 can be injection molded or machined from a billet material. Body 104, impaction head 108 and lever 110 can be machined from metals. Handle 106 can include a metal component that is overmolded with a plastic or rubber material.

A method for implanting cup 102 into a patient can include obtaining or providing the cup and obtaining or providing adapter inserter 100. As disclosed herein, protuberance 506 can be placed into a recess of cup 102 as shown in FIGS. 1B and 1C. As disclosed herein, placing protuberance 506 into the recess of cup 102 does not require rotation of adapter inserter 100 or cup 102. As cup 102 is secured to adapter inserter 100, protuberance 506 can engage an indentation in cup 102 without having to rotate, sometimes referred to as clocking, cup 102 and/or adapter inserter 100.

Cup 102 can be secured to collet 320 of adapter insert 100 by rotating lever 110 from an unlocked position as shown in FIG. 1B to a locked position as shown in FIG. 1C. Securing cup 102 to collet 320 by rotating lever 110 can include retracting collet spreader 318 into collet cavity 508 as disclosed herein. Securing cup 102 to collet 320 by rotating lever 110 can include causing exterior surface such as flared surface 402 of collet spreader 318 to contact interior surface 504 of collet 320, thereby causing collet 320 to expand as disclosed herein. Securing cup 102 to collet 320 can cause cup 102 to be pulled towards first end 116 of body 104 as disclosed herein.

Implanting cup 102 can also include striking impact head 108 of adapter inserter 100 to implant cup 102 in the patient. Once implanted, collet 320 can be disengaged from cup 102 by rotating lever 110 from the locked position shown in FIG. 1C to the unlocked position shown in FIG. 1B. Disengaging collet 320 from cup 102 can include causing a portion of collet spreader 318, such as flared surface 402, contacting interior surface 504 of collet 320 to protrude from a distal end of collet 320. Finally, adapter inserter 100 can be withdrawn from the patient, thereby leaving cup 102 within the patient.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for implanting an acetabular cup implant, the system comprising:
   a body including a first end;
   a first linkage coupled to the body at the first end;
   a collet connectable to the first end of the body, the collet including an exterior surface and an interior surface, the exterior surface defining a protuberance sized to engage an indentation in an adapter, the interior surface defining a collet cavity; and
   a collet spreader connectable to a first end of the first linkage, the collet spreader including a flared surface located at a first end of the collet spreader and arranged to contact the interior surface of the collet upon retraction of the collet spreader into the collet cavity; and
   a first cam connected to the first linkage,
   wherein rotation of the first cam in a first direction causes retraction of the collet spreader into the collet cavity,
   wherein, upon retraction of the collet spreader into the collet cavity, the collet expands and the protuberance engages the indentation in the adapter.

2. The system of claim 1, further comprising:
   a lever connected to the body;
   a second cam; and
   a second linkage coupling the first cam to the second cam, wherein actuation of the lever causes rotation of the first cam via movement of the second linkage and the second cam.

3. The system of claim 1, further comprising a biasing element located within the collet cavity and arranged to exert an outward force on the collet spreader.

4. The system of claim 1, wherein the interior and exterior surfaces of the collet define:
   a plurality of slots proximate a first end of the collet; and
   a relief opening at a base of each of the plurality of slots.

5. The system of claim 1, wherein the protuberance is a helical thread.

6. The system of claim 1, wherein the protuberance is one of a plurality of protuberances.

7. An adapter inserter comprising:
   a body having a proximal end and a distal end;
   a first linkage located at the distal end;
   a second linkage extending from the proximal end to the distal end;
   a first cam connecting the first linkage to the second linkage wherein rotation of the first cam cause linear motion of the first linkage;
   a lever connected to the body and defining a second cam connected to the second linkage;
   a collet spreader connected to the first linkage and comprising a flared surface located at a first end of the collet spreader; and
   a collet connected to the distal end of the body and encircling a portion of the collet spreader, the collet comprising:
      a protuberance extending from an exterior surface and sized to engage an indentation in an adapter, and
      an interior surface defining a collet cavity,
   wherein actuation of the lever causes
      rotation of the first cam via movement of the second linkage and the second cam, and
      the flared surface of the collet spreader to contact the interior surface of the collet, thereby causing the collet to expand and the protuberance to engage the indentation in the adapter.

8. The adapter inserter of claim 7, further comprising a biasing element located within the collet cavity and arranged to exert an outward force on the collet spreader.

9. The adapter inserter of claim 7, wherein the interior and exterior surfaces of the collet define:
   a plurality of slots proximate a first end of the collet; and
   a relief opening at a base of each of the plurality of slots.

10. The adapter inserter of claim 7, wherein the protuberance is a helical thread.

11. The adapter inserter of claim 7, wherein the protuberance is one of a plurality of protuberances.

12. A method for implanting an acetabular cup implant in a patient, the method comprising:
   obtaining or providing the acetabular cup implant;
   obtaining or providing an adapter inserter comprising a collet and a body, the collet connectable to a first end of a body of the adapter inserter
   placing a protuberance of the collet into a recess of the acetabular cup;
   securing the acetabular cup to the collet by rotating a lever of the adapter inserter from an unlocked position to a locked position without rotating the adapter inserter or the collet;

striking an impact head of the adapter inserter to implant the acetabular cup in the patient;

disengaging the collet from the acetabular cup by rotating the lever of the adapter inserter from the locked position to the unlocked position, wherein securing the acetabular cup to the collet includes rotating a first cam connected to a first linkage connected to a collect spread such that rotation of the first cam in a first direction causes retraction of the collet spreader into the collet cavity.

13. The method of claim 12, wherein securing the acetabular cup to the collet by rotating the lever comprises retracting a collet spreader into a collet cavity defined by the collet, thereby causing the collet to expand.

14. The method of claim 12, wherein securing the acetabular cup to the collet by rotating the lever cause an exterior surface of a collet spreader to contact an interior surface of the collet, thereby causing the collet to expand.

15. The method of claim 12, wherein securing the acetabular cup to the collet by rotating the lever comprises causing a flared surface located at a first end of a collet spreader to contact an interior surface of the collet, thereby causing the collet to expand.

16. The method of claim 12, wherein securing the acetabular cup to the collet by rotating the lever comprises causing the acetabular cup to be pulled towards the first end of the body of the adapter inserter.

17. The method of claim 12, wherein placing the protuberance of the collet into the recess of the acetabular cup does not require rotation of the adapter inserter or the acetabular cup.

18. The method of claim 12, wherein disengaging the collet from the acetabular cup by rotating the lever from the locked position to the unlocked position comprises causing a portion of a collet spreader contacting an interior surface of the collet to protrude from a distal end of the collet.

19. The method of claim 12, further comprising withdrawing the adapter inserter from the patient, thereby leaving the acetabular cup within the patient.

* * * * *